US00PP36939P3

(12) United States Plant Patent
Kamstra

(10) Patent No.: US PP36,939 P3
(45) Date of Patent: Sep. 2, 2025

(54) ***LAVANDULA* PLANT NAMED 'LAAZ0014'**

(50) Latin Name: *Lavandula angustifolia*
Varietal Denomination: LAAZ0014

(71) Applicant: SYNGENTA CROP PROTECTION AG, Basel (CH)

(72) Inventor: Silvan Adelmar Kamstra, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/785,097

(22) Filed: Jul. 26, 2024

(65) Prior Publication Data

US 2025/0212710 P1 Jun. 26, 2025

(30) Foreign Application Priority Data

Nov. 16, 2023 (QZ) ..... PBR 2023/2395

(51) Int. Cl.
*A01H 6/50* (2018.01)
*A01H 5/02* (2018.01)

(52) U.S. Cl.
USPC ..... Plt./445
CPC ..... *A01H 6/502* (2018.05); *A01H 5/02* (2013.01)

(58) Field of Classification Search
USPC ..... Plt./445
CPC ..... A01H 6/502; A01H 5/02
See application file for complete search history.

*Primary Examiner* — Keith O. Robinson
(74) *Attorney, Agent, or Firm* — Dale Skalla

(57) ABSTRACT

A new *Lavandula* plant named 'LAAZ0014' particularly distinguished by dark purple-blue flowers, a very long flower spikes, dark green foliage, very abundant flowering, large sized plants with a well-branched, relatively tight and upright habit.

1 Drawing Sheet

Latin name of the genus and species of the plant claimed: *Lavandula angustifolia.*

Varietal denomination: 'LAAZ0014'.

BACKGROUND OF THE NEW PLANT

The present invention comprises a new *Lavandula*, botanically known as *Lavandula angustifolia*, and hereinafter referred to by the variety name 'LAAZ0014'.

'LAAZ0014' is a product of a planned breeding program. The new cultivar has purple-blue flowers, a very long flowering season, dark green foliage, very abundant flowering, relative large spikes, relatively tight and upright habit. The plant is tolerant to cold, but main use will be for summer production.

'LAAZ0014' originated from a pollination made in July 2019 in a greenhouse in Enkhuizen, The Netherlands.

The female parent was the unpatented, proprietary plant designated 'LAVAY2354-5', with blue violet flowers, small spikes, greyish foliage and abundant flowering compared to 'LAAZ0014'.

The male parent of 'LAAZ0014' was the unpatented, proprietary plant designated 'LAVAY2265-17', with blue violet flowers, large spikes, green foliage and a tight and narrow habit compared to 'LAAZ0014'.

The resultant seed was sown in January 2020 and grown outdoors in Enkhuizen, The Netherlands. 'LAAZ0014' was selected as a single flowering plant within the progeny of the stated cross in June 2020 in Enkhuizen, The Netherlands.

The first act of asexual reproduction of 'LAAZ0014' was accomplished when vegetative stem cuttings were propagated from the initial selection July 2020 in a greenhouse in Enkhuizen, The Netherlands.

BRIEF SUMMARY OF INVENTION

Horticultural examination of plants grown from cuttings of the plant initiated in July 2020, and continuing thereafter, has demonstrated that the combination of characteristics as herein disclosed for 'LAAZ0014' are firmly fixed and are retained through successive generations of asexual reproduction.

'LAAZ0014' has not been observed under all possible environmental conditions. The phenotype may vary significantly with variations in environment such as temperature, light intensity and day length.

A Plant Breeder's Right for this cultivar was applied for in the European Union on Nov. 16, 2023, No. 2023/2395. 'LAAZ0014' has not been made publicly available prior to the effective filing date of this application, notwithstanding any disclosure that may have been made less than one year prior to the effective filing date of this application by the inventor or another who obtained 'LAAZ0014' directly from the inventor.

The following traits have been repeatedly observed and are determined to be basic characteristics of the new variety. The combination of these characteristics distinguishes this *Lavandula* as a new and distinct variety.

BRIEF DESCRIPTION OF THE PHOTOGRAPHS

The accompanying photographic drawings show typical flower and foliage characteristics of 'LAAZ0014' with colors being as true as possible with an illustration of this type.

Figure 1:
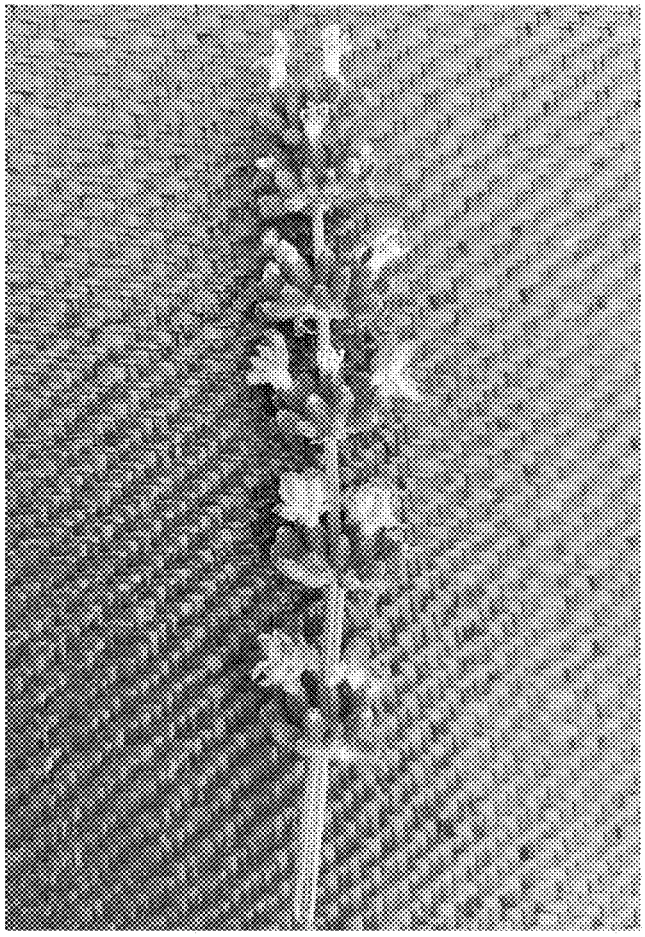
Figure 2:
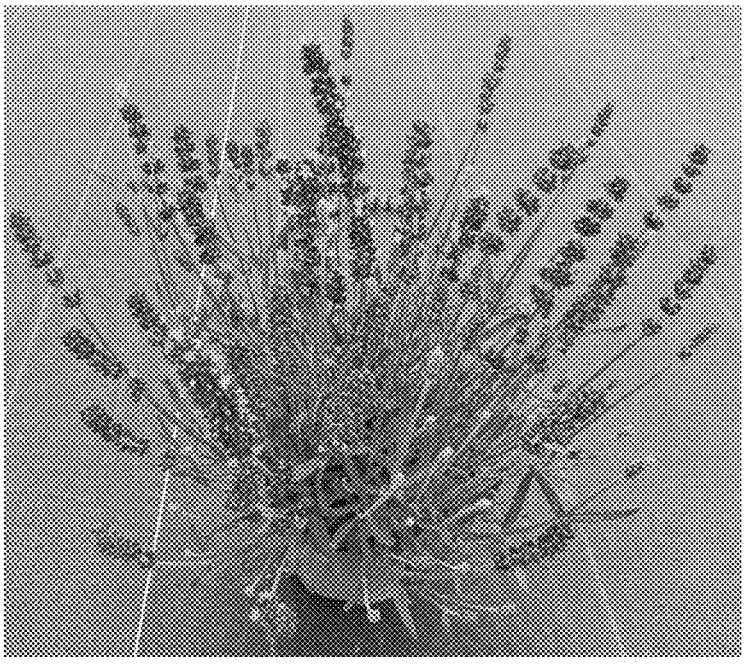

The photographic drawings show in FIG. 1 a close view of an inflorescence and in FIG. 2 a whole flowering plant from an outdoor trial.

DETAILED BOTANICAL DESCRIPTION

The plant descriptions and measurements were taken outdoors in Enkhuizen, The Netherlands on Jul. 25, 2024 on about 21 week old plants. Rooted cuttings had been planted, one plant per pot, in 13 cm pots in week 10, 2024. The plants were pinched.

Color references are made to The Royal Horticultural Society Colour Chart (R.H.S.) 2001.

TABLE 1

DIFFERENCES BETWEEN THE NEW VARIETY 'LAAZ0014' AND A MOST SIMILAR VARIETY

| | 'LAAZ0014' | 'LAAZ0005', U.S. Pat. No. PP27447 |
|---|---|---|
| Flowering response: | About 1 week later to start | Bit earlier |
| Cold resistance: | Good | Poor |
| Amount of flowers: | More flower spikes >50 | Less flowers |
| Length of peduncle: | Up to 15 cm | Up to 7 cm |

Plant:
- *Form, growth and habit.*—Compact, upright, freely branching.
- *Plant height.*—25-30 cm.
- *Plant height (inflorescence included).*—About 30 cm.
- *Plant width.*—About 30 cm.

Roots:
- *Number of days to initiate roots.*—About 13 days at about 20 degrees C.
- *Number of days to produce a rooted cutting.*—4-5 weeks at 18 degrees C.
- *Type.*—Fine, fibrous, free branching.
- *Color.*—Closest RHS 155D.

Foliage:
- *Type.*—Opposite; decussate, sessile.
- *Fragrance.*—Very strong.
- *Immature, leaf color, upper surface.*—RHS 138A.
- *Lower surface.*—RHS 138B.
- *Mature, leaf color, upper surface.*—RHS 137A.
- *Lower surface.*—RHS 137B.
- *Length.*—3.5-5.0 cm.
- *Width.*—0.6 cm.
- *Shape.*—Linear.
- *Base shape.*—Sessile.
- *Apex shape.*—Acute.
- *Margin.*—Entire.
- *Texture, upper surface.*—Smooth.
- *Lower surface.*—Smooth.
- *Color of veins, upper surface.*—RHS 143C.
- *Color of veins, lower surface.*—RHS 143C.

Stem:
- *Number of main stems per plant.*—About 30.
- *Color of stem.*—RHS 138A.
- *Length of stem.*—About 20-25 cm.
- *Diameter.*—0.4 cm.
- *Length of internodes.*—1-5 cm.
- *Shape of stem.*—Square.
- *Strength.*—Good.
- *Texture.*—Slightly Pubescent.
- *Peduncle color.*—RHS 137C.
- *Peduncle length.*—About 12.0 cm.
- *Peduncle diameter.*—0.3 cm.
- *Peduncle strength.*—Strong.
- *Peduncle texture.*—Slightly Pubescent.

Inflorescence:
- *Flowering season.*—From June until October.
- *Type.*—Flowers in compact spikes, terminal on stems; flowers stay open all day.
- *Number of open flowers per spike.*—About 20, but this varies a lot depending on the development stage.
- *Quantity of inflorescences per plant.*—About 30.
- *Lastingness of individual blooms on the plant.*—About 4 days.

Bud (when first showing color):
- *Color.*—RHS 93A.
- *Length.*—0.4 cm.
- *Width.*—0.3 cm.
- *Shape.*—Oval.

Corolla:
- *Immature, color of petals, upper surface.*—RHS 93A.
- *Immature, color of petals, lower surface.*—RHS 93A.
- *Spike horizontal diameter.*—2.2 cm.
- *Spike height.*—9.5 cm.
- *Mature, color of petals, upper surface.*—RHS 91A.
- *Mature, color of petals, lower surface.*—RHS 91A.
- *Petal length.*—0.3 cm.
- *Petal diameter.*—0.2 cm.
- *Apex.*—Obtuse.
- *Margin.*—Entire.
- *Shape.*—Rounded.
- *Base.*—Fused.
- *Degree of lobation.*—Moderate.
- *Texture, upper surface.*—Glabrous.
- *Texture, lower surface.*—Glabrous.
- *Corolla tube, color, outer surface.*—RHS 91A and RHS 155B.
- *Corolla tube, color, inner surface.*—RHS 91D and RHS 155B.
- *Corolla tube length.*—0.7 cm.
- *Diameter (at opening).*—0.2 cm.
- *Corolla tube texture, outer surface.*—Glabrous.
- *Corolla tube texture, inner surface.*—Glabrous.

Calyx:
- *Form.*—All sepals fused to form tube around the corolla.
- *Color.*—RHS 90A.
- *Length of tube.*—0.6 cm.
- *Width of tube.*—0.2 cm.
- *Texture, outer surface.*—Pubescent.
- *Texture, inner surface.*—Glabrous.

Reproductive organs:
- *Number of stamens.*—4.
- *Filament color.*—RHS 155C.
- *Filament length.*—0.2 cm.
- *Filament diameter.*—0.05 cm.
- *Anther color.*—RHS N167A.
- *Anther length.*—0.05 cm.
- *Anther shape.*—Reniform.
- *Pollen color.*—RHS 163B.
- *Pollen amount.*—Sparse.
- *Pistil.*—1 per flower.
- *Pistil length.*—0.4 cm.
- *Style color.*—RHS 150D.
- *Style length.*—0.2 cm.
- *Stigma color.*—RHS N199C.

Fertility/seed set: Has not been observed.

Disease/pest resistance: Has not been observed.

What is claimed is:

1. A new and distinct cultivar of *Lavandula* plant named 'LAAZ0014', as substantially illustrated and described herein.

* * * * *